(12) United States Patent
Lim et al.

(10) Patent No.: US 10,994,054 B2
(45) Date of Patent: *May 4, 2021

(54) SCAFFOLD FOR LIVING DONOR TRANSPLANTATION

(71) Applicants: CG Bio Co., Ltd., Seongnam-si (KR); BioAlpha Inc., Seoul (KR)

(72) Inventors: Jun Young Lim, Seoul (KR); Yong Bok Kim, Gwangju-si (KR); Hyun Seung Ryu, Yongin-si (KR)

(73) Assignees: CG BIO CO., LTD., Seongnam-si (KR); BIOALPHA INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/710,073

(22) Filed: Dec. 11, 2019

(65) Prior Publication Data

US 2021/0023275 A1    Jan. 28, 2021

(30) Foreign Application Priority Data

Jul. 25, 2019   (KR) .................. 10-2019-0090063
Nov. 25, 2019   (KR) .................. 10-2019-0151855

(51) Int. Cl.

| | | |
|---|---|---|
| *A61L 27/10* | (2006.01) | |
| *B33Y 10/00* | (2015.01) | |
| *A61L 27/56* | (2006.01) | |
| *A61L 27/54* | (2006.01) | |
| *B33Y 70/00* | (2020.01) | |
| *B33Y 80/00* | (2015.01) | |

(52) U.S. Cl.
CPC .............. *A61L 27/56* (2013.01); *A61L 27/10* (2013.01); *A61L 27/54* (2013.01); *A61L 2430/02* (2013.01); *B33Y 10/00* (2014.12); *B33Y 70/00* (2014.12); *B33Y 80/00* (2014.12)

(58) Field of Classification Search
CPC .......... A61L 27/56; A61L 27/10; A61L 27/54; A61L 2430/02; B33Y 80/00; B33Y 10/00; B33Y 70/00
See application file for complete search history.

(56) References Cited

U.S. PATENT DOCUMENTS

| | | |
|---|---|---|
| 2012/0093895 A1 | 4/2012 | Song et al. |
| 2016/0297935 A1 | 10/2016 | Reese et al. |
| 2018/0327552 A1 | 11/2018 | Reese et al. |
| 2018/0370165 A1 | 12/2018 | Hikmet et al. |

(Continued)

FOREIGN PATENT DOCUMENTS

| | | |
|---|---|---|
| KR | 10-2016-0094803 | 8/2016 |
| KR | 1020170148259 | 11/2017 |

(Continued)

OTHER PUBLICATIONS

Eqtesadi et al. (Journal of the European Ceramic Society 2015;35:3985-3993). (Year: 2015).*

(Continued)

*Primary Examiner* — Ernst V Arnold
(74) *Attorney, Agent, or Firm* — Lex IP Meister, PLLC

(57) ABSTRACT

Disclosed is a scaffold for living donor transplantation, which includes sintered bioglass and a biocompatible polymer and has improved properties using a 3D printer through a fused deposition modeling process.

10 Claims, 8 Drawing Sheets

Specification includes a Sequence Listing.

(56) References Cited

U.S. PATENT DOCUMENTS

2019/0299520 A1  10/2019  Wieber et al.

FOREIGN PATENT DOCUMENTS

| KR | 10-2018-0128227 | 12/2018 |
| KR | 10-1912839 | 12/2018 |

OTHER PUBLICATIONS

Eqtesadi et al. (Materials Letters 2013;93:68-71) (Year: 2013).*
Fonseca et al. (Biomater Sci 2018;6:1569-1579). (Year: 2018).*
YongBok Kim et al., "3D-printed PCL/bioglass (BGS-7) composite scaffolds with high toughness and cell-responses for bone tissue regeneration", Journal of Industrial and Engineering Chemistry, vol. 79, Nov. 25, 2019, pp. 163-171.
KIPO, Office Action of KR 10-2019-0151855 dated Dec. 16, 2019.
Xin Qi et al., "Mesoporous bioactive glass-coated 3D printed borosilicate bioactive glass scaffolds for improving repair of bone defects", International Journal of Biological Sciences, 2018; 14(4): 471-484. doi: 10.7150/ijbs.23872.
KIPO, Final Office Action of KR 10-2019-0090063 dated Mar. 25, 2020.
KIPO, Office Action of KR 10-2019-0090063 dated Dec. 12, 2019.
KIPO, Office Action of KR 10-2019-0151855 dated Apr. 27, 2020.

* cited by examiner

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: runx2 forward primer

<400> SEQUENCE: 1
acatccccat ccatccat                                                 18

<210> SEQ ID NO 2
<211> LENGTH: 20
<212> TYPE: DNA
<213> ORGANISM: Artificial Sequence
<220> FEATURE:
<223> OTHER INFORMATION: runx2 reverse primer

<400> SEQUENCE: 2
ggtgctgggt tctgaatctg                                               20

<210> SEQ ID NO 3
```

```
<211> LENGTH: 18
<212> TYPE: DNA
<213> ORGANISM: Artificial Sequence
<220> FEATURE:
<223> OTHER INFORMATION: OPN forward primer

<400> SEQUENCE: 3
ggaggaaacc agccaagg                                                 18

<210> SEQ ID NO 4
<211> LENGTH: 22
<212> TYPE: DNA
<213> ORGANISM: Artificial Sequence
<220> FEATURE:
<223> OTHER INFORMATION: OPN reverse primer

<400> SEQUENCE: 4
tgccagaatc agtcactttc ac                                            22

<210> SEQ ID NO 5
<211> LENGTH: 20
<212> TYPE: DNA
<213> ORGANISM: Artificial Sequence
<220> FEATURE:
<223> OTHER INFORMATION: OCN forward primer

<400> SEQUENCE: 5
ccctcctgaa ggtctcacaa                                               20

<210> SEQ ID NO 6
<211> LENGTH: 20
<212> TYPE: DNA
<213> ORGANISM: Artificial Sequence
<220> FEATURE:
<223> OTHER INFORMATION: OCN reverse primer

<400> SEQUENCE: 6
gctgtctccc tcatgtgttg                                               20

<210> SEQ ID NO 7
<211> LENGTH: 20
<212> TYPE: DNA
<213> ORGANISM: Artificial Sequence
<220> FEATURE:
<223> OTHER INFORMATION: Col-I forward primer

<400> SEQUENCE: 7
actcagccgt ctgtgcctca                                               20

<210> SEQ ID NO 8
<211> LENGTH: 20
<212> TYPE: DNA
<213> ORGANISM: Artificial Sequence
<220> FEATURE:
<223> OTHER INFORMATION: Col-I reverse primer

<400> SEQUENCE: 8
ggaggcctcg gtggacatta                                               20

<210> SEQ ID NO 9
<211> LENGTH: 19
<212> TYPE: DNA
<213> ORGANISM: Artificial Sequence
<220> FEATURE:
<223> OTHER INFORMATION: ALP forward primer

<400> SEQUENCE: 9
```

```
gcccagtgcc ttctgattt                                              19

<210> SEQ ID NO 10
<211> LENGTH: 20
<212> TYPE: DNA
<213> ORGANISM: Artificial Sequence
<220> FEATURE:
<223> OTHER INFORMATION: ALP reverse primer

<400> SEQUENCE: 10
gggcagcgtc agatgttaat                                             20

<210> SEQ ID NO 11
<211> LENGTH: 20
<212> TYPE: DNA
<213> ORGANISM: Artificial Sequence
<220> FEATURE:
<223> OTHER INFORMATION: BMP2 forward primer

<400> SEQUENCE: 11
agatctgtac cgcaggcact                                             20

<210> SEQ ID NO 12
<211> LENGTH: 19
<212> TYPE: DNA
<213> ORGANISM: Artificial Sequence
<220> FEATURE:
<223> OTHER INFORMATION: BMP2 reverse primer

<400> SEQUENCE: 12
gttcctccac ggcttcttc                                              19

<210> SEQ ID NO 13
<211> LENGTH: 22
<212> TYPE: DNA
<213> ORGANISM: Artificial Sequence
<220> FEATURE:
<223> OTHER INFORMATION: GAPDH forward primer

<400> SEQUENCE: 13
ccttgagatc aacacgtacc ag                                          22

<210> SEQ ID NO 14
<211> LENGTH: 19
<212> TYPE: DNA
<213> ORGANISM: Artificial Sequence
<220> FEATURE:
<223> OTHER INFORMATION: GAPDH reverse primer

<400> SEQUENCE: 14
cgcctgtaca ctccaccac                                              19
```

SCAFFOLD FOR LIVING DONOR TRANSPLANTATION

BRIEF DESCRIPTION OF THE DRAWINGS CROSS REFERENCE TO RELATED APPLICATION(S)

This application claims the benefit of and priority to Korean Patent Application Nos. 10-2019-0090063 filed Jul. 25, 2019 and 10-2019-0151855 filed Nov. 25, 2019, both of which are currently pending and incorporated herein by reference in their entirety.

TECHNICAL FIELD

The present invention relates to a scaffold for living donor transplantation.

DESCRIPTION OF THE RELATED ART

A 3D printer is a device for fabricating a product having the same three-dimensional shape as an actual product by melting a material such as a polymer, metal, etc. or stacking powder based on a 3D drawing.

A 3D printer has the advantage of making it easy to shape and fabricate a product having a complicated structure according to the intended design, and thus, the application of early versions thereof is gradually expanding and the market is expected to expand further.

3D-printing technology in medical and biotechnological fields is applied to 3D bio-printing, which produces artificial organs such as livers, kidneys, hearts, etc. from bio-ink, tissue engineering for regeneration of artificial tissues or organs, and personalized medicine.

3D-printing technology is fundamentally classified into a total of 7 types depending on the 3D digital model: photopolymerization (PP), material extrusion (ME), binder jetting (BJ), material jetting (MJ), direct energy deposition (DED), powder bed fusion (PBF), and sheet lamination (SL).

In particular, fused direct deposition (hereinafter referred to as 'FDM'), which is a material-jetting process, is widely used.

FDM is a 3D-printing process in a manner in which an injectable thin-filament-type resin is melted in a nozzle, extruded, and stacked layer by layer. Here, the nozzle melts the plastic filament at a high temperature, and the extruded filament is cured at room temperature to thus form a strut.

An FDM-type 3D printer is a technology to which a variety of materials may be applied and which may exhibit superior accuracy and repeatability, whereby the fabricated product is robust and has high durability and excellent dimensional stability.

The applicability of FDM-type 3D-printing technology to medical and biotechnological fields is very high, and, in particular, thorough research into a scaffold for living donor transplantation is ongoing.

Korean Patent No. 10-1912839 discloses an FDM 3D printer composition in a paste form, including a ceramic powder composed mainly of CaO and $SiO_2$ and a binder, thus making it possible to quickly fabricate shaped products without a melting process and to precisely realize various geometric structures to thereby be useful as a bio-substitute for medical use.

However, the ceramic powder is problematic in that it may be easily broken or cracked even by external pressure or impact due to inherent brittleness thereof. Moreover, a natural polymer, which is used as the binder, has superior biocompatibility and does not cause cytotoxicity, but has weak mechanical strength and difficult processing.

For the application to a scaffold for living donor transplantation, the issues of mechanical properties and biocompatibility must be solved first, in addition to the technology of precisely processing the geometric structure of the scaffold.

Citation List

Patent Literature

Korean Patent No. 10-1912839

DISCLOSURE

Technical Problem

Accordingly, the present invention has led to the development of a novel composition that is able to overcome the brittleness problems, in which, when the composition is applied to an FDM 3D-printing process to produce a scaffold for living donor transplantation, both toughness and stiffness may be increased and surface properties may be improved, thus simultaneously achieving mechanical materials and biological activity required of a scaffold.

Therefore, an objective of the present invention is to provide a scaffold for living donor transplantation.

Technical Solution

The present invention provides a scaffold for living donor transplantation, configured such that struts, which are essentially disposed on top of each other and cross each other in a vertical direction to thus form pores therein, are stacked layer by layer.

Here, the struts may include bioglass and a biocompatible polymer, and may have a stack structure of two or more layers.

The struts may be provided in an interconnected or disconnected form in the same layer and may be formed parallel in a regular pattern including a linear shape, a corrugated shape, a lattice shape, a zigzag shape or a spiral shape, or in an irregular pattern.

Also, the struts may have a diameter of 300 μm to 500 μm.

Also, the struts may have an average orientation angle of 30° to 60° between layers.

The scaffold for living donor transplantation may have a bimodal pore size distribution and a porosity of 30% to 60%, and may satisfy the following properties:

(1) toughness: 50 $kPa/mm^3$ to 850 $kPa/mm^3$
(2) stiffness: 1.5 N/mm to 20 N/mm
(3) roughness ($R_a$): 130 nm to 260 nm
(4) water contact angle after 180 sec: 75° or less
(5) protein proliferation absorbance after 24 hr: 0.25 to 0.6 O.D.
(6) cell-seeding efficiency: 37% or more
(7) cell proliferation absorbance after culture for 7 days: 0.22 O.D. or more
(8) F-actin area ratio: 22% or more The bioglass constituting the struts may be sintered bioglass.

Moreover, the scaffold for living donor transplantation may be fabricated by mixing the sintered bioglass and the biocompatible polymer and then performing injection molding.

Here, injection molding may be performed using a 3D printer through a fused deposition modeling process.

Advantageous Effects

According to the present invention, a scaffold for living donor transplantation is configured to include sintered bioglass and a biocompatible polymer at an optimal content ratio, and can thus exhibit optimal toughness and stiffness, whereby conventional problems such as cracking and the like due to inherent brittleness of bioglass can be solved.

Also, the scaffold for living donor transplantation has improved surface properties and hydrophilic properties and can thus exhibit high protein absorption ability upon living donor transplantation, and moreover, has an effect of activating cell proliferation and bone formation, and is thereby preferably applicable as a scaffold required in medical and biotechnological fields.

DETAILED DESCRIPTION OF THE INVENTION

A layer-by-layer (LBL) stacking process is performed to obtain a 3D product by stacking one layer on another. The present invention pertains to a scaffold for living donor transplantation fabricated using an LBL stacking process.

Specifically, the scaffold for living donor transplantation of the present invention is configured such that struts, which are essentially disposed on top of each other and cross each other in a vertical direction to thus form pores therein, are stacked layer by layer.

The external shape and dimension of the scaffold for living donor transplantation may be selected so as to be suitable for individual applications, and may meet the purpose required in the application field. The scaffold for living donor transplantation may have an external shape selected from among an extended shape, for example, a cylindrical shape, a polygonal column shape such as a triangular prism shape or an ingot shape, a planar shape, a polygonal shape, for example, a rectangular shape, a cubic shape, a square shape, a pyramid shape, a pentagonal shape, a 12-gonal shape, a 20-gonal shape, a rhombohedral shape, a prismatic shape, a spherical shape, for example, a ball shape, a hollow shape, a protruded lens shape or a cylindrical lens shape, and a disc shape or an annular shape. This shape may be achieved by stacking struts.

Figure 1:
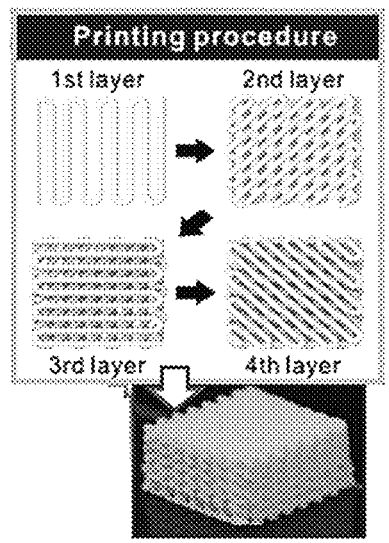
FIG. 1 shows an example of a strut stack according to the present invention.

FIG. 1 illustrates the strut stack according to an embodiment of the present invention. For sake of convenience, a rectangular-parallelepiped-shaped scaffold for living donor transplantation is disclosed in the present invention.

The struts constituting the scaffold for living donor transplantation are provided in multiple layers, including at least two layers, three or more layers, four or more layers and n or more layers, and the number of layers thereof may vary depending on the end use of the scaffold. Preferably, when struts are stacked in four or more layers to form a scaffold, it is advantageous for ensuring the properties required of the scaffold.

A single strut layer is configured such that a filament of substantially a single composition is extended, and also includes a structure in a disconnected form, such as a lattice pattern. The struts may be formed to extend in various shapes in the same layer and may be formed in a regular pattern such as a linear shape, a corrugated shape, a lattice shape, a zigzag shape or a spiral shape, or in an irregular pattern, in order to increase the contact area with cells and fluids. Preferably, the formation of a regular pattern, such as a lattice shape, is advantageous for controlling the properties and porosity of the scaffold.

Also, in order to satisfy the properties required of the scaffold, the struts may have a diameter of 300 μm to 500 μm, 350 μm to 470 μm, or 380 μm to 450 μm. More preferably, the diameter thereof ranges from 390 μm to 425 μm. If the diameter thereof is less than the above lower limit, it is difficult to ensure properties such as strength due to the low thickness thereof. On the other hand, if the diameter thereof exceeds the above upper limit, the pores are relatively small in size and are unable to achieve sufficient porosity for cell growth or fluid flow.

The struts stacked in two or more layers are configured such that adjacent layers are arranged to be rotated by a predetermined angle to thus form an orientation angle between these layers. As will be explained later, struts are formed through an injection-molding process, in which injection may be performed using a nozzle mounted on a 3D transfer mechanism, the position of which is adjusted in three directions, namely XYZ directions. Thus, the "direction" mentioned below means the injection direction.

For example, in the case of a structure in which struts are stacked in four layers, the first layer is formed in parallel at a regular spacing in the X-axis direction, and the second layer is formed in parallel at a regular spacing at a predetermined angle relative to the X axis of the first layer. Here, the layer formed in parallel in the second layer is reset to the X' axis, and the third layer is formed in parallel at a predetermined angle relative to the X' axis. Further, the layer formed in parallel in the third layer is reset to the X" axis, and the fourth layer is formed in parallel at a predetermined angle relative to the X" axis.

Such an orientation angle may be referred to as a rotation angle, and the average orientation angle between the layers of n-layered struts may fall in the range of 5° to 355°, 10° to 350°, 15° to 345°, or 20° to 330°. More preferably, it falls in the range of 5° to 180°, 5° to 160°, or 10° to 150°. The average orientation angle is an orientation angle between layers, and when a four-layered structure is configured such that layers are arranged at a layer orientation angle of 60°, the orientation angle between the first layer and the fourth layer may be 180°. The orientation angle is an average numeric value, and in the n-layered structure, the orientation angle between the layers may be formed equally or unequally.

In regard to the orientation angle, based on the first layer, the second layer may have an orientation angle of 5° to 180° relative to the first layer and the third layer may have an orientation angle of 10° to 340° relative to the first layer. As such, the orientation angle between the first layer and the $n^{th}$ layer may range from 0° to 360°.

According to an embodiment of the present invention, in the structure of struts stacked in four layers, the second layer may be arranged to be rotated by 30° to 60° relative to the first layer, the third layer may be arranged to be rotated by 75° to 105° relative to the first layer, and the fourth layer may be arranged to be rotated by 120° to 150° relative to the first layer.

According to another embodiment of the present invention, in the structure of struts stacked in four layers, the second layer may be arranged to be rotated by 40° to 50° relative to the first layer, the third layer may be arranged to be rotated by 85° to 95° relative to the first layer, and the fourth layer may be arranged to be rotated by 130° to 140° relative to the first layer.

Due to the aforementioned arrangement of the struts, the struts constituting individual layers cross each other, thereby forming pores therein. The pores are largely classified into two or more types, for example, pores formed by stacking struts in a vertical direction and pores formed by the spacing between struts arranged in the same strut layer. The pore size may vary depending on the stack structure and the spacing, and the pores have a plurality of pore distributions having the same or different pore sizes, such as bimodal and trimodal distributions. Moreover, the inter-pore regions may be independently formed, or may be in the form of vertically connected channels (i.e. interconnected pore structures) to enable free movement of the fluid.

If the struts are stacked outside the above angular range, the mechanical properties of the resulting scaffold for living donor transplantation may be deteriorated, and moreover, it may be difficult to control the pore size and porosity thereof, thus being unsuitable for living donor transplantation. Hence, when the struts are arranged in multiple layers through relative rotation as described above, it is possible to fabricate a scaffold having a geometrically stacked structure and to attain mechanical properties and effects such as cell growth and the like by virtue of the above structure.

According to an embodiment of the present invention, in the structure of struts stacked in four layers, the scaffold for living donor transplantation has a bimodal pore distribution having first pores having a size of 380 μm to 430 μm, and preferably 410 μm to 420 μm, and second pores having a size of 200 μm to 250 μm. Here, the porosity of the scaffold for living donor transplantation may vary depending on the type of stacking of struts and the diameter thereof, but may fall in the range of 30% to 60%, 35% to 55%, 40% to 50%, or 40% to 45%.

The pore size and porosity of the scaffold for living donor transplantation may fall within ranges that facilitate cell proliferation, cell differentiation and bone formation, and moreover, may be freely adjusted within the above ranges so as to enable movement of fluids and attachment of cells for tissue regeneration therethrough, to prevent cell loss to thus control cell engraftment rate, and to meet the requirements for properties of the scaffold for living donor transplantation.

The scaffold for living donor transplantation according to the present invention may be applied in a variety of fields.

A conventional scaffold for living donor transplantation may be fabricated through various methods, among which an injection-molding process using a 3D printer based on FDM technology is performed in the present invention.

In order to attain the properties required of the scaffold for living donor transplantation through the FDM process, the following two considerations should be kept in mind: application to the FDM process has to be possible, and the properties (e.g. biocompatibility, strength, etc.) of the scaffold fabricated by the FDM process have to be superior.

In the present invention, the use of a mixture of sintered bioglass and a biocompatible polymer is capable of solving the problem of biocompatibility, and the stack structure of the struts makes it possible to achieve desired properties, particularly stiffness and strength.

Stiffness refers to a property whereby deformation does not occur in response to external force, and toughness refers to a property of resisting strong impacts. When both are improved, the scaffold for living donor transplantation does not easily crack by virtue of the increased resistance to pressure or impact, which may compensate for the brittleness of the ceramic material of bioglass.

Toughness measurement is performed through a 3-point bending test, and three parameters are obtained: toughness, maximum bending moment and maximum bending stress.

The toughness may fall in the range of 50 kPa/mm$^3$ to 850 kPa/mm$^3$, 70 kPa/mm$^3$ to 800 kPa/mm$^3$, or 100 kPa/mm$^3$ to 800 kPa/mm$^3$, and preferably ranges from 600 kPa/mm$^3$ to 800 kPa/mm$^3$.

Here, the maximum bending moment may fall in the range of 25 N·mm to 70 N·mm, 30 N·mm to 65 N·mm, or 35 N·mm to 650 N·mm, and preferably ranges from 45 N·mm to 60 N·mm.

Moreover, the maximum bending stress may fall in the range of 3 MPa to 9 MPa, 3.5 MPa to 8.5 MPa, or 4 MPa to 8 MPa, and preferably ranges from 4.5 MPa to 7.5 MPa.

Stiffness may be measured using a compression tester, and three parameters are obtained: stiffness, yield displacement and yield stress.

The stiffness may fall in the range of 1.5 N/mm to 20 N/mm, 1.8 N/mm to 15 N/mm, or 2.0 N/mm to 10 N/mm, and preferably ranges from 2.0 N/mm to 5 N/mm.

The yield displacement may fall in the range of 0.3 mm to 0.8 mm or 0.35 mm to 0.7 mm, and preferably ranges from 0.4 mm to 0.65 mm.

The yield stress may fall in the range of 3 MPa to 20 MPa, 4 MPa to 15 MPa, or 4.5 MPa to 10 MPa, and preferably ranges from 5 MPa to 10 MPa.

In addition to the aforementioned properties, the scaffold for living donor transplantation of the present invention also has surface properties and various activities such as bioactivity and the like mentioned below.

For example, the roughness ($R_a$) of the surface of the scaffold measured using a surface roughness meter (Nanoview-m4151p, Korea) may fall within a range of 130 nm to 260 nm, 135 nm to 250 nm, or 140 nm to 240 nm.

Also, the water contact angle, associated with hydrophilicity, has the following numerical value. The water contact angle is measured using a sessile drop process at room temperature (25° C.) by placing 10 μL of a water droplet on the scaffold surface, and lower values thereof indicate greater hydrophilicity.

After 1 sec: 90° or less, 40° to 90°, 70° or less, 43° to 70°
After 30 sec: 80° or less, 0° to 80°, 60° or less, 20° to 60°
After 180 sec: 75° or less, 0° to 75°, 30° or less, 10° to 30°

Also, the scaffold for living donor transplantation of the present invention has a range of 0.19 to 0.6 O.D. (optical density) in view of absorbance associated with protein absorption ability using a BCA (Bicinchoninic acid) protein assay (Pierce Kit, Thermo Scientific), and has the following range over time.

After 1 hr (O.D.): 0.19 or more, 0.19 to 0.27, 0.22 to 0.25
After 6 hr (O.D.): 0.23 or more, 0.23 to 0.38, 0.26 to 0.35
After 12 hr (O.D.): 0.24 or more, 0.24 to 0.43, 0.30 to 0.39
After 24 hr (O.D.): 0.25 or more, 0.25 to 0.60, 0.40 to 0.59

Cell-seeding efficiency, a parameter related to cell activity, may be represented by a numeric value of 37% or more, 40% or more, or 45% or more. The higher the above numeric value, the better the cell adhesion, growth, and differentiation, which means that cell activity is increased.

Moreover, the scaffold for living donor transplantation of the present invention has cell proliferation absorbance in the following range after 7-day culture related to the cell proliferation rate measured using a cell proliferation assay (MTT Assay). Here, a higher numeric value means that cell proliferation is occurring efficiently.

After 1 day (%): 0.17 or more, 0.19 or more, 0.19 to 0.3
After 3 days (%): 0.19 or more, 0.21 or more, 0.21 to 0.3
After 7 days (%): 0.22 or more, 0.25 or more, 0.25 to 0.4

Furthermore, the F-Actin area ratio of the scaffold for living donor transplantation according to the present invention may fall in the range of 22% or more, 25% or more, 28% or more, 28% to 60%, or 30% to 55%.

In addition, the scaffold for living donor transplantation according to the present invention is fabricated by a) mixing sintered bioglass and a biocompatible polymer and b) performing injection molding.

These steps are described in detail below.

a) Mixing

The properties of the scaffold described above may be achieved through mixing of sintered bioglass and biocompatible polymer and control of the content ratio therebetween.

Bioglass, which is one of bioceramics, is a bioactive ceramic that is embedded in living bodies and forms a strong chemical bond by directly contacting the surrounding bone without a fibrous film therearound.

Bioglass may be selected from the group consisting of CaO, $SiO_2$, $P_2O_5$, $B_2O_3$ and combinations thereof.

The bioglass of the present invention may be selected from the group consisting of CaO, $SiO_2$, $P_2O_5$, $B_2O_3$ and combinations thereof, and is non-toxic and has the effect of inducing osteoblast differentiation in human mesenchymal stem cells better than hydroxyapatite, which is the basic mineral of bone. It also has twice the compressive strength of hydroxyapatite and may thus be used as a biocompatible material in the intervertebral space.

CaO is a material that is easily fused with other ceramic components to thus contribute to the fluidity, durability and water resistance of the entire composition, and the amount of CaO is preferably 20 to 60 wt %, and more preferably 40 to 50 wt %, based on the total weight of the bioglass, but the present invention is not limited thereto. If the amount of CaO is less than 20 wt % based on the total weight of the bioglass, durability and water resistance of 3D-printed products may decrease. On the other hand, if the amount of CaO exceeds 60 wt % based on the total weight of the bioglass, the brittleness of 3D-printed products may increase, or the fluidity of the entire composition is poor, thus non-uniformly extruding the composition upon 3D printing, which is undesirable.

$SiO_2$ is a material that has transparency, viscosity, durability, and a low fusion temperature and contributes to stabilization of the entire composition, and the amount of $SiO_2$ is preferably 15 to 40 wt %, and more preferably 30 to 40 wt %, based on the total weight of the bioglass, but the present invention is not limited thereto. When the amount of $SiO_2$ falls within the above range, bioactivity may be improved and glass crystallization may become good.

$P_2O_5$ may inhibit the growth of bacteria such as Streptococcus mutans and may thus increase bioactivity. In particular, $P_2O_5$, which is contained in a large amount in natural teeth or bones, is able to form a glass matrix and to increase the permeability thereof. The amount of $P_2O_5$ is preferably 6 to 20 wt %, and more preferably 12 to 16 wt %, based on the total weight of the bioglass, but the present invention is not limited thereto. If the amount of $P_2O_5$ is less than 6 wt % based on the total weight of the bioglass, the effect of inhibiting bacterial propagation and the formation of the glass matrix become insignificant. On the other hand, if the amount of $P_2O_5$ exceeds 20 wt %, brittleness may increase, which is undesirable.

$B_2O_3$ may improve glass crystallization to thus further increase mechanical strength and thermal expansion rate. The amount of $B_2O_3$ is preferably 1 wt % or less, and more preferably 0.5 wt % or less, based on the total weight of the bioglass, but the present invention is not limited thereto.

In particular, the bioglass of the present invention uses a material crystallized through sintering, rather than using the material having the above composition as it is.

Specifically, the bioglass is subjected to crystallization through sintering, thus making it possible to enhance the intrinsic strength and hardness of a 3D-printed product to be fabricated.

The sintering temperature may be variously altered in consideration of the intrinsic glass transition temperature of bioglass. For example, during the sintering process, the heating step may be performed in a manner in which the temperature is gradually elevated at a heating rate of 0.01 to 0.8° C./min so as to reach a peak temperature of 800 to 1200° C., after which sintering may be carried out for 160 to 200 min at the peak temperature. A drastic change in temperature makes it difficult to maintain the shape of the sintered bioglass injected using the 3D printer, thus causing cracks and voids and significantly reducing strength.

During the sintering process, the cooling step may be performed in a manner in which the temperature of the shaped product is gradually lowered from the peak temperature to 10 to 35° C. at a cooling rate of 0.01 to 0.8° C./min. If the temperature is lowered at a cooling rate exceeding 0.8° C./min, cracks or voids may form, thus significantly reducing strength.

The peak temperature of the sintering process affects the strength of the final scaffold, and sintering is preferably carried out at 800 to 1200° C. in order to realize a substitute for hard biotissue. If the peak temperature is lower than 800° C., compressive strength may decrease, making the scaffold incapable of serving as a substitute for hard biotissue. On the other hand, if the peak temperature is higher than 1200° C., cracking may occur.

The sintering process is performed after the injection-molding process in the fabrication of the scaffold for living donor transplantation, and thus, in the case in which non-sintered bioglass is used, rather than sintered bioglass, the resulting scaffold is configured such that the sintered bioglass alone is left behind without the biocompatible polymer. In this case, due to the high brittleness thereof, cracks are easily generated under external impact or pressure, making it unsuitable for use as a scaffold.

Also, the biocompatible polymer, which is mixed with the sintered bioglass, functions as a binder. The binder is responsible for binding fine particles of sintered bioglass to each other to make them cohesive and viscous, and allows the bioglass to have excellent toughness to thus overcome the inherent brittleness problem. Moreover, when the composition composed of the sintered bioglass and the biocompatible polymer functioning as a binder, which are mixed together, is melted, the composition is imparted with fluidity and flowability to thus facilitate injection.

A representative example of the biocompatible polymer may be selected from the group consisting of poly(ε-caprolactone) (PCL), polyethylene (PE), poly(methyl methacrylate) (PMMA), polylactic acid (PLA), poly-L-lactic acid (PLLA), polyglycolide (PGA), polylactic-co-glycolic acid (PLGA), polyvinyl chloride (PVC), polytetrafluoroethylene (PTFE), polyethylene terephthalate (PET), polyurethane, polyacetal, polyamide, polyamide elastomer, polyester, polyester elastomer, polypropylene, polyacrylonitrile, polysulfone, polyorthoester, polyanhydride, chitosan, gelatin, collagen and combinations thereof.

The biocompatible polymer according to the present invention is preferably a biodegradable polymer. The biodegradable polymer enables control of the mechanical strength thereof, is easy to process, and enables the biodegradation rate thereof to be adjusted depending on the synthesis conditions, so the material may be efficiently utilized. Preferably, the biodegradable polymer is any one selected from the group consisting of poly(ε-caprolactone), polylactic acid, poly-L-lactic acid, polyglycolide, polylactic-co-glycolic acid and combinations thereof, and more preferably poly(ε-caprolactone) is used.

In particular, the amounts of the sintered bioglass and the biocompatible polymer are controlled in order to satisfy not only the toughness and stiffness of the scaffold but also the properties, such as surface roughness, hydrophilicity, protein absorption ability, and the like.

Specifically, the amount of the sintered bioglass is 10 to 70 wt %, preferably 30 to 50 wt %, and more preferably 35 to 45 wt %, based on the total weight of the composition. If the amount of the sintered bioglass is less than the above lower limit, the intrinsic mechanical properties of bioglass, such as compressive strength, etc., may decrease. On the other hand, if the amount thereof exceeds the above upper limit, it is difficult to inject the resulting composition due to the high viscosity thereof.

Also, the amount of the biocompatible polymer may be 30 to 90 wt %, 50 to 70 wt %, or 55 to 65 wt % based on the total weight of the composition. If the amount of the biocompatible polymer is less than the above lower limit, insufficient bonding force between sintered bioglass particles may result, or it may be difficult to solve the problem of brittleness of the sintered bioglass. On the other hand, if the amount thereof exceeds the above upper limit, the relative amount of the sintered bioglass is low, and thus there is a concern that the properties of the scaffold that is ultimately fabricated may decrease.

In addition, the content ratio of the sintered bioglass and the biocompatible polymer is related to the viscosity (η*, complex viscosity) in the fabrication of a scaffold using an FDM 3D printer. Specifically, the sintered bioglass has a non-viscoelastic characteristic, and the viscosity of a melt upon injection molding increases with an increase in the amount thereof. The high-viscosity melt may affect the shape and process quality of the struts after injection molding, making it difficult to ensure the diameter or thickness uniformity of the struts, and the nozzle may become clogged. The appropriate viscosity range may be obtained through the above content ratio of the sintered bioglass and the biocompatible polymer, and the viscosity preferably falls in the range of 110 to 800 Pa·s, 120 to 700 Pa·s, or 150 to 500 Pa·s.

The sintered bioglass may be pulverized before or after sintering. In particular, the average particle size of the sintered bioglass after pulverization is adjusted to the range of 1.5 to 2.5 μm. Here, the average particle size is calculated from the value measured using a particle size analyzer (APA2000, MALVERN) (a cumulative 50% point in the average diameter distribution of the particles).

The pulverization process may be performed using any known pulverizer, for example, a freezer mill.

In order to uniformly mix the sintered bioglass and the biocompatible polymer, the biocompatible polymer may be used after first being pulverized to a particle size range similar to that of the sintered bioglass, or the pulverization process may be performed during the mixing process.

b) Injection Molding

Next, the pulverized composition is injection-molded to fabricate a scaffold for living donor transplantation.

Injection molding may be performed through an FDM 3D-printing process.

An FDM (fused deposition modeling) 3D printer is a kind of 3D printer that fabricates a three-dimensional shaped product by injecting and stacking a material having fluidity and flowability through a melting process, and includes currently commercially available FDM 3D printers and FFF (fused filament fabrication) 3D printers.

The composition for an FDM 3D printer according to the present invention is in the form of a paste having fluidity, flowability and viscosity. Specifically, the composition for an FDM 3D printer according to the present invention may be applied to all 3D printers, regardless of the type thereof, so long as the 3D printer is any 3D printing device capable of injection, in addition to being applicable to commercially available FDM and FFF 3D printers.

The heater provided to the 3D printer operates in a temperature range of 25 to 250° C. and functions to melt the pulverized composition. When the sintered bioglass and the biocompatible polymer, which are solid, are melted and formed into a paste, the composition may be imparted with fluidity and flowability to thus facilitate injection.

In order to increase the identity or similarity of the geometric size of the struts through injection molding, optimization of processing parameters such as nozzle speed, pneumatic pressure and heating temperature is required.

Figure 2A:
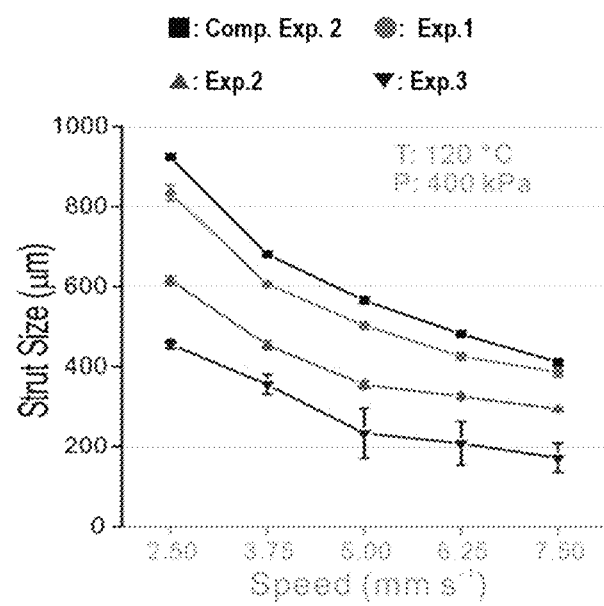
FIGS. 2(a) to 2(d) are graphs showing changes in the properties of struts depending on the processing parameters in Examples 1 to 3 and Comparative Examples 1 and 2.

As the nozzle speed (mm/s) increases, the strut size (μm) of each scaffold may decrease. For example, as shown in FIG. 2(a), showing the results of testing at a temperature of 120° C. and a pneumatic pressure of 400 kPa, the strut size may decrease with an increase in the nozzle speed. Also, in order to produce struts having the same size, the nozzle speed may decrease with an increase in the amount of sintered bioglass.

Figure 2B:
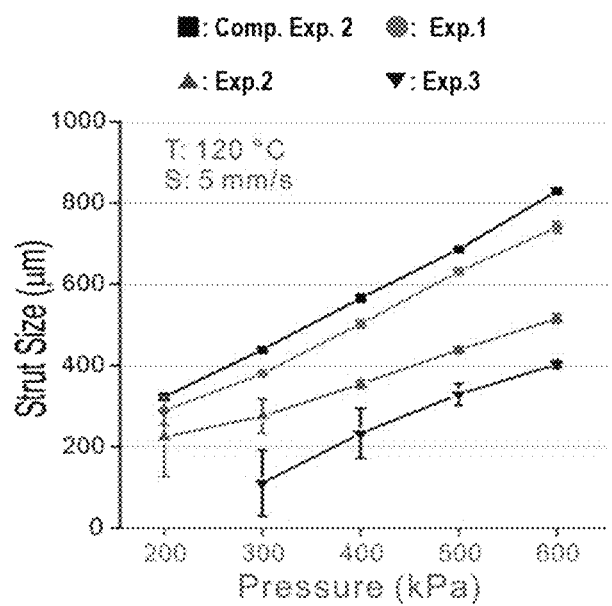

Also, as the pneumatic pressure (kPa) increases, the strut size (μm) of each scaffold may increase. For example, as shown in FIG. 2(b), showing the results of testing at a temperature of 120° C. and a nozzle speed of 5 mm/s, the strut size may increase with an increase in the pneumatic pressure due to the high flow rate and low viscosity of the composition. Also, in order to produce struts having the same size, the pneumatic pressure may increase with an increase in the amount of sintered bioglass.

Figure 2C:
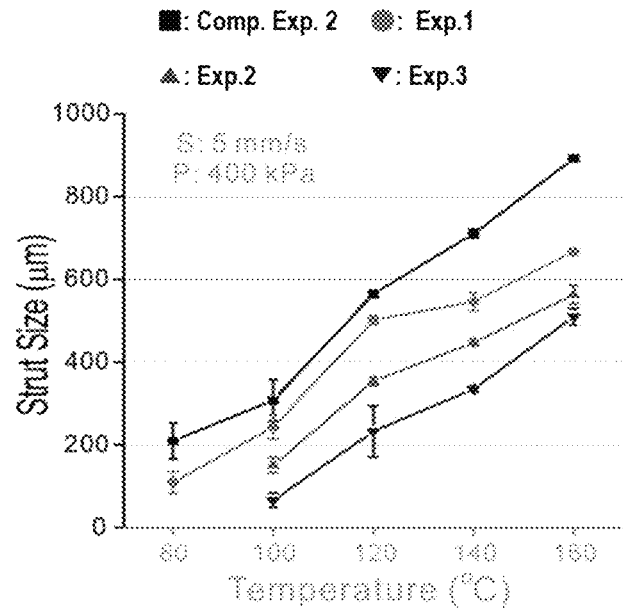

As the temperature (° C.) increases, the strut size (μm) of each scaffold may increase. For example, as shown in FIG. 2(c), showing the results of testing at a nozzle speed of 5 mm/s and a pneumatic pressure of 400 kPa, the strut size may increase with an increase in the temperature due to the high flow rate and low viscosity of the composition. Also, in order to produce struts having the same size, the temperature may increase with an increase in the amount of sintered bioglass.

In a conventional fabrication of a scaffold for living donor transplantation, the sintering process is performed after injection molding, but may be excluded in the present invention because of the use of sintered bioglass and biocompatible polymer. Accordingly, the fabrication process may be simplified and the cost thereof may be reduced.

The scaffold for living donor transplantation according to the present invention may be used for artificial bones, artificial joints, oral maxillofacial bones, skulls or dental artificial roots, and may be utilized as a disc-shaped artificial bone for use in spinal fusion or an artificial bone for use in facial reconstruction.

EXAMPLES

A better understanding of the present invention will be given through the following examples, which are merely set forth to illustrate the present invention but are not to be construed as limiting the scope of the present invention.

Preparation Example 1

Preparation of Sintered Bioglass 139.8 g of CaO, 113.7 g of $SiO_2$, 45.6 g of $P_2O_5$, and 0.9 g of $B_2O_3$, which were dry powder, were placed in a vessel and mixed to afford 300 g of bioglass.

The bioglass thus obtained was sintered under the following conditions, thereby obtaining sintered bioglass.

(Sintering Conditions)
0→600° C.: 720 min
600° C. (Holding): 60 min
600→1000° C.: 800 min
1000° C. (Holding): 180 min
1000→600° C. and 600° C. (Holding): 800 min
600→20° C.: 720 min Examples and Comparative Examples Fabrication of Scaffold for Living Donor Transplantation (1) Mixing The bioglass obtained in Preparation Example 1 was placed in a ball mill (High-Energy Ball Mill, FRITSCH) and pulverized so as to have an average particle size of 2.1 μm. The bioglass thus pulverized was mixed with poly(ε-caprolactone) (PURASORB PC12, Corbion Purac, hereinafter referred to as 'PCL') at the content ratio shown in Table 1 below, thus preparing 100 g of a composition.

The composition thus prepared was placed in a freezer mill (6875D, SPEX Sampleprep) and pulverized so as to have an average particle size of 2.1 μm.

(2) Injection Molding

The composition thus pulverized was melted using a heater provided to an FDM 3D printer (DTR3-3315-EX, Dasa Robot System). Subsequently, the composition in a paste phase was loaded in a nozzle in the printer (diameter: 500 ∞m), after which the composition was injected to a size of 6×6×2 $mm^3$ via the injection port and stacked layer by layer on the working table.

Here, a scaffold composed of struts stacked in four directions, as shown in FIG. 1, was fabricated by crossing the second layer at an injection direction of 45°, the third layer at an injection direction of 90° and the fourth layer at an injection direction of 135°, based on the direction of injection of the first layer upon injection-molding of the composition in a layer-by-layer manner.

TABLE 1

|  | Sintered bioglass (wt %) | PCL (wt %) | Melting temp. (° C.) | Processing time (min) | Nozzle speed (mm/s) | Pneumatic pressure (kPa) |
| --- | --- | --- | --- | --- | --- | --- |
| Example 1 | 20 | 80 | 120 | 2 | 5 | 320 |
| Example 2 | 40 | 60 | 120 | 2 | 5 | 450 |
| Example 3 | 60 | 40 | 140 | 2 | 5 | 500 |
| Comparative Example 1 | 100 | 0 | 25 | 2 | 5 | 430 |
| Comparative Example 2 | 0 | 100 | 100 | 2 | 5 | 480 |

Test Example 1

Determination of Processing Parameter

Optimal processing parameters were determined by testing the speed, pneumatic pressure, temperature and viscosity during the injection-molding process using the compositions of Examples 1 to 3.

FIGS. 2(a) to 2(d) are graphs showing changes in the properties of struts depending on the processing parameters in Examples 1 to 3 and Comparative Examples 1 and 2.

As shown in FIGS. 2(a) to 2(c), the diameter of struts was affected by the nozzle speed, the amount of sintered bioglass, and the melting temperature. For example, as the amount of the sintered bioglass was increased, the diameter of the struts was smaller, and as the pneumatic pressure and the amount of bioglass were increased, the diameter of the struts was larger.

Figure 2D:
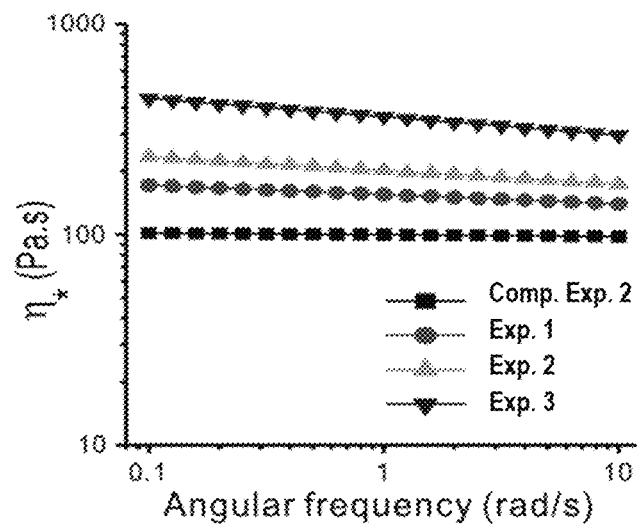

The viscosity of FIG. 2(d) was measured using a rotational rheometer provided in the form of a parallel plate having a diameter of 20 mm and a gap therein of 2 mm (Bohlin Gemini HR Nano, Malvern Instruments, Surrey, UK), and the frequency sweep was carried out at a strain of 1% and 140° C. With reference to FIG. 2(d), the viscosity was increased with an increase in the amount of the sintered bioglass.

Based on the results of FIG. 2, processing conditions suitable for the optimal strut diameter (390 to 425 μm) for use in a scaffold for living donor transplantation were set by adjusting the amounts of sintered bioglass/PCL, and were applied to the processing conditions of the Examples.

Test Example 2

Analysis of Strut Structure (1) Pore Characteristics

The scaffolds fabricated in Examples 1 to 3 and Comparative Examples 1 and 2 were measured for strut diameter, pore size and porosity. The results thereof are shown in Table 2 below. The pore size was measured using a scanning electron microscope (SEM, SNE-3000M, SEC Inc., Korea), and the porosity was calculated using the following equation and bulk density ($\rho$) (PCL (1.135 g/cm$^3$)/bioglass (3.05 g/cm$^3$)).

$$\text{Porosity (\%)} = (1 - (1/\rho_s) \times (W_s/V_a)) \times 100 \quad \text{[Equation 1]}$$

($\rho$: bulk density, $W_s$: weight of the structure, $V_a$: volume of the structure)

TABLE 2

| | Strut diameter (μm) | 1$^{st}$ pore size (μm) | 2$^{nd}$ pore size (μm) | Porosity (%) |
|---|---|---|---|---|
| Example 1 | 424.3 ± 7.7 | 400.7 ± 10.2 | 214.3 ± 14.1 | 42.5 ± 2.1 |
| Example 2 | 401.4 ± 16.3 | 415.7 ± 14.4 | 222.9 ± 16.7 | 43.1 ± 1.0 |
| Example 3 | 420.7 ± 9.2 | 412.1 ± 7.0 | 216.4 ± 20.5 | 42.3 ± 1.2 |
| Comparative Example 1 | 392.5 ± 20.1 | 391.5 ± 9.1 | 207.7 ± 20.7 | 46.8 ± 3.0 |
| Comparative Example 2 | 400.7 ± 4.7 | 439.3 ± 14.3 | 221.4 ± 13.6 | 43.1 ± 1.5 |

As is apparent from Table 2, the struts had a diameter of 390 to 425 μm, a bimodal pore size distribution, and a porosity of 42 to 47%.

(2) Microscope Analysis

Figure 3:
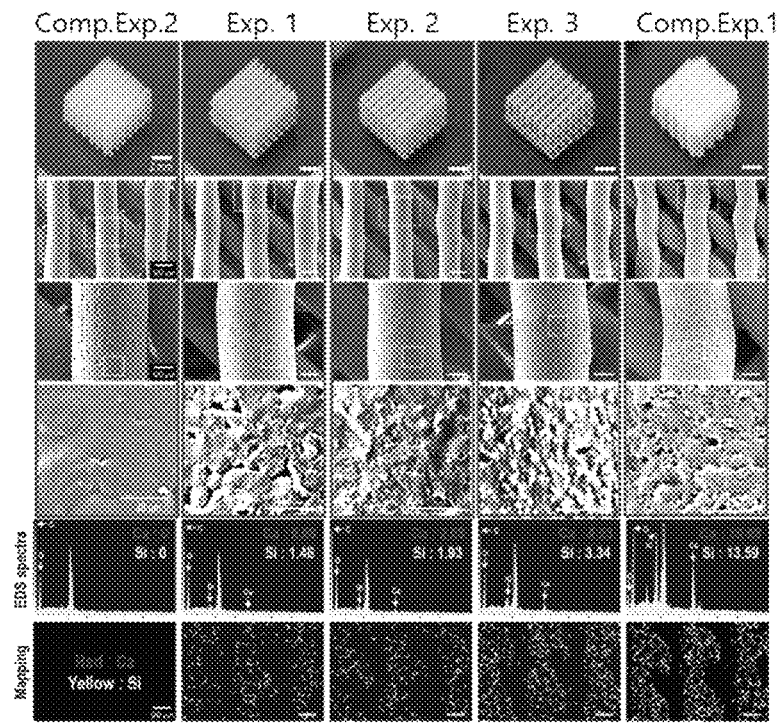
FIG. 3 shows scaffolds and struts fabricated in Examples 1 to 3 and Comparative Examples 1 and 2.

FIG. 3 shows the scaffolds and struts fabricated in Examples 1 to 3 and Comparative Examples 1 and 2.

The first line of FIG. 3 shows optimal microscope (BX FM-32, Olympus, Tokyo, Japan) images, in which the scaffold was configured to include struts stacked in four layers.

The second line to the fourth line of FIG. 3 show scanning electron microscope (SEM, SNE-3000M, SEC Inc., Korea) images, in which the multilayered struts are disposed at predetermined rotation angles and pores are formed in the surface thereof. The pores in the surface of the struts provide a rough surface that can promote cell adhesion and bone tissue differentiation upon tissue regeneration.

The fifth line and the sixth line of FIG. 3 show the results of energy dispersive spectroscopy (EDS) with a field emission scanning electron microscope (JSM7500F, JEOL LTD.) and the distribution mapping of Ca and Si. As is apparent from these images, it can be confirmed that the struts contain Ca and Si and that the concentrations of Ca and Si in the struts are increased with an increase in the amount of the bioglass.

Test Example 3

Analysis of Composition

The compositions (after pulverization) used to fabricate the scaffolds of Examples 1 to 3 and Comparative Examples 1 and 2 were subjected to thermogravimetric analysis and X-ray diffraction. The results thereof are shown in FIGS. 4(a) and 4(b).

(1) Thermogravimetric Analysis (TGA)

10 mg of each composition was heated from 30° C. to 800° C. at a heating rate of 20° C./min, and was then subjected to TGA using a thermogravimetric analyzer (TGA-2050, TA-Instruments) in a nitrogen atmosphere.

Figure 4A:
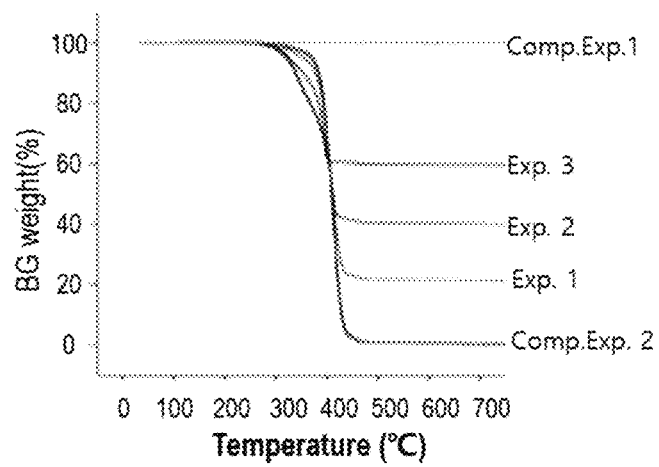
FIGS. 4(a) and 4(b) are graphs showing the results of thermogravimetric analysis and X-ray diffraction of compositions for use in fabricating scaffolds of Examples 1 to 3 and Comparative Examples 1 and 2.
Figure 4B:
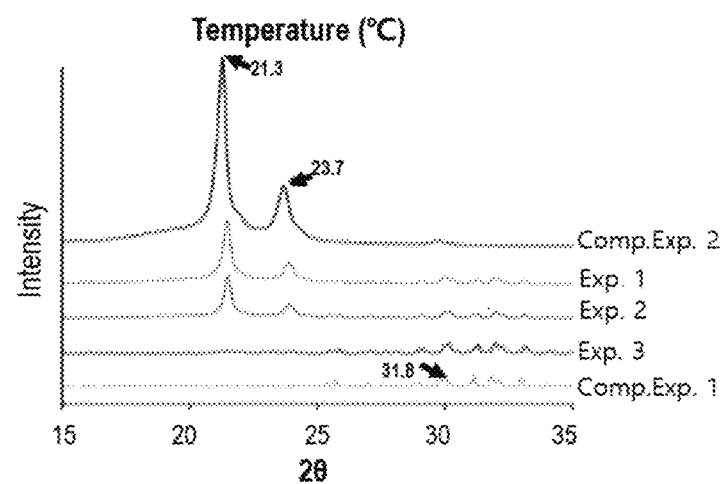

FIG. 4(a) is a TGA graph of the compositions used to fabricate the scaffolds of Examples 1 to 3 and Comparative Examples 1 and 2. As shown in FIG. 4(a), in Comparative Example 1, using only the sintered bioglass, there was no change in the weight due to the absence of PCL, and in Comparative Example 2, using only PCL, complete pyrolysis occurred at 500° C. In contrast, in the compositions of Examples 1 to 3, it was confirmed that sintered bioglass that was mixed was left behind in an amount corresponding to the weight thereof.

(2) X-Ray Diffraction (XRD)

In order to measure the crystal size, an X-ray diffractometer (Siemens D500 WAXD, Siemens) using CuK$_\alpha$ radioactive rays under beam conditions of 40 kV and 20 mA was used. The X-ray diffraction test was performed under conditions of 2θ=15-35° and a step size of 0.1°.

FIG. 4(b) shows the XRD spectra of the compositions used to fabricate the scaffolds of Examples 1 to 3 and Comparative Examples 1 and 2. As shown in FIG. 4(b), the strongest peaks were observed at 2θ=21.3° and 23.7°, corresponding to the crystal planes (110) and (200) of PCL of Comparative Example 2. In Comparative Example 1, the peak was observed at 2θ=31.8°, corresponding to the crystal plane (211) of the hydroxyapatite structure in the sintered bioglass.

In contrast, in the compositions of Examples 1 to 3, the above peaks were included, indicating that the sintered bioglass and PCL were appropriately mixed in the compositions.

Test Example 4

Analysis of Properties of Scaffold

Figure 5A:
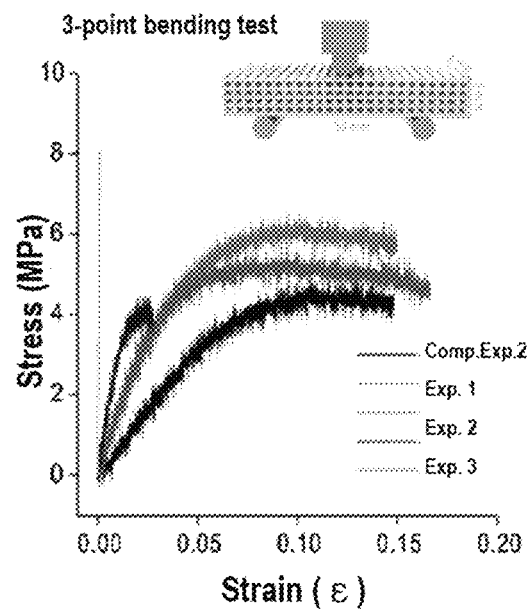
FIGS. 5(a) and 5(b) are graphs showing the results of testing of toughness and compression of the compositions for use in fabricating scaffolds of Examples 1 to 3 and Comparative Examples 1 and 2.
Figure 5B:
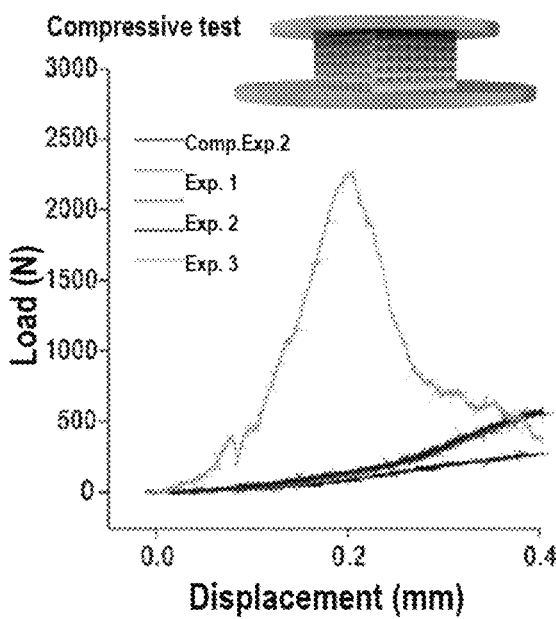
Figure 6A:
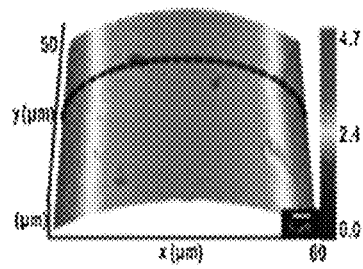
FIGS. 6(a) to 6(e) show 3D surface topographical images of the scaffolds fabricated in Examples 1 to 3 and Comparative Example 1.
Figure 6B:
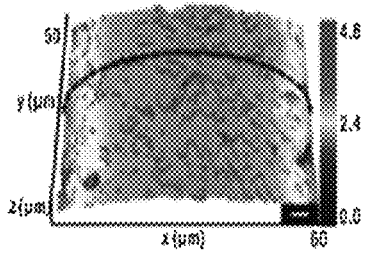
Figure 6C:
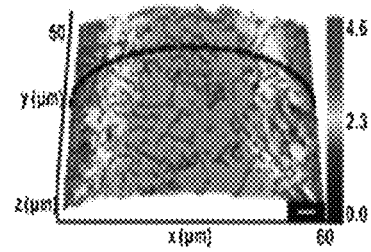
Figure 6D:
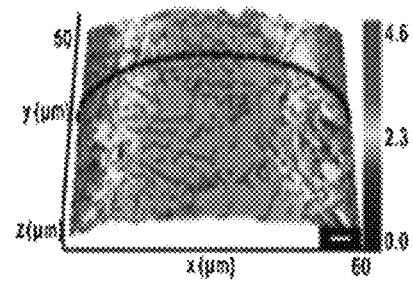
Figure 6E:
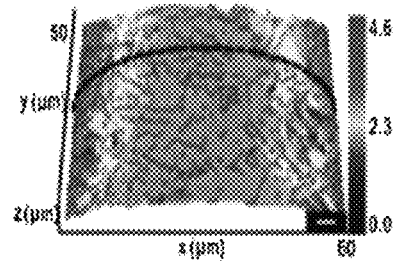

In order to evaluate the toughness-related properties of the scaffolds fabricated in Examples 1 to 3 and Comparative Examples 1 and 2, the following testing for toughness and stiffness was performed. The results thereof are shown in Table 3 below and in FIGS. 5(a) and 5(b).

Maximum bending moment, maximum bending stress and toughness: Bending testing was performed using a 3-point bending tester at a speed of 0.5 mm/min (MTS Bionix Tabletop Test System, MTS System Corp., MN, USA), specimen (30×4×3 mm$^3$ size)

Stiffness, yield displacement and yield stress: Measurement was performed using a compressive strength meter at a compression rate of 0.5 mm/min (MTS Bionix Tabletop Test System, MTS System Corp., MN, USA), specimen (10×10×5 mm$^3$ size)

TABLE 3

|  |  | Example 1 | Example 2 | Example 3 | Comparative Example 1 | Comparative Example 2 |
|---|---|---|---|---|---|---|
| 3-Point bending test | Max. Bending moment (N/mm) | 55.8 ± 0.5 | 47.6 ± 0.9 | 38.1 ± 0.5 | 74.7 ± 6.8 | 37.3 ± 1.8 |
|  | Max. Bending stress (MPa) | 6.3 ± 0.1 | 5.6 ± 0.2 | 4.3 ± 0.2 | 7.8 ± 0.7 | 4.6 ± 0.2 |
|  | Toughness (kPa/mm$^3$) | 760 ± 41.7 | 710 ± 5.48 | 100 ± 22.7 | 5.9 ± 0.9 | 480 ± 46.2 |
| Compression test | Stiffness (N/mm) | 2.5 ± 0.1 | 2.9 ± 0.1 | 2.9 ± 0.2 | 25.9 ± 6.3 | 1.1 ± 0.1 |
|  | Yield displacement (mm) | 0.6 ± 0.03 | 0.5 ± 0.04 | 0.5 ± 0.06 | 0.2 ± 0.01 | 0.4 ± 0.02 |
|  | Yield stress (MPa) | 6.1 ± 0.2 | 6.6 ± 0.1 | 5.8 ± 0.6 | 21.2 ± 5.8 | 2.6 ± 0.2 |

As is apparent from Table 3 and FIG. 5, in the scaffold of Comparative Example 1 using the sintered bioglass alone, stiffness was very high but toughness was very low. Also, in the scaffold of Comparative Example 2 using PCL alone, stiffness was low and toughness was high, in contrast with Comparative Example 1.

In order to serve for a scaffold for living donor transplantation, the stiffness and toughness values have to be appropriately balanced, rather than being unbalanced, as in Comparative Examples 1 and 2. Therefore, it can be concluded that the scaffolds of Examples 1 to 3 simultaneously satisfy toughness of about 50 to 850 (kPa/mm$^3$) and stiffness of 2 to 3 N/m.

Test Example 5

Analysis of Surface Properties of Scaffold (1) Measurement of Surface Roughness/3D Surface Topographical Images The 3D surface topographical images were obtained using a phase shift interferometer, and thus the surface roughness of the scaffolds was analyzed. As shown in FIGS. 6(a) to 6(e), the scaffolds of Examples 1 to 3 and Comparative Example 1 had a rougher surface.

For qualitative analysis of such roughness, the surface roughness ($R_a$) was obtained based on the following equation using a surface roughness meter (Nanoview-m4151p, Korea).

$$R_a = [\int |Z(x)| dx]/L \text{ ($Z$ and $L$ of FIGS. 6($a$) to 6($e$) are the height and length of the rough structure)} \quad \text{[Equation 2]}$$

TABLE 4

|  | Surface roughness ($R_a$) (unit: nm) |
|---|---|
| Example 1 | 144.7 ± 31.9 |
| Example 2 | 168.1 ± 26.3 |
| Example 3 | 234.3 ± 41.7 |
| Comparative Example 1 | 284.6 ± 55.4 |
| Comparative Example 2 | 118.5 ± 14.9 |

As is apparent from Table 4, compared to Comparative Example 2 using the biocompatible polymer alone, when the amount of the bioglass that was contained was higher, the surface roughness was increased, indicating that the surface roughness can be adjusted depending on the content ratio of sintered bioglass/PCL.

(2) Measurement of Water Contact Angle

The hydrophilicity of the scaffolds fabricated in Examples 1 to 3 and Comparative Examples 1 and 2 was evaluated using a water contact angle meter. The results thereof are shown in Table 5 below.

Hydrophilicity evaluation was carried out by placing 10 μL of a water droplet on each scaffold surface and measuring a water contact angle using a sessile drop process at room temperature (25° C.).

TABLE 5

| Water contact angle | 1 sec | 30 sec | 180 sec |
|---|---|---|---|
| Example 1 | 67 ± 2° | 58 ± 5° | 26 ± 3° |
| Example 2 | 46 ± 3° | 34 ± 4° | 20 ± 3° |
| Example 3 | 45 ± 2° | 26 ± 3° | 14 ± 3° |
| Comparative Example 1 | 39 ± 3° | 0° | 0° |
| Comparative Example 2 | 93 ± 4° | 82 ± 4° | 78 ± 3° |

As is apparent from Table 5, compared to Comparative Example 2 (78±3°) using PCL alone, the contact angle was decreased with an increase in the amount of the sintered bioglass. The scaffold of Example 1, containing 20 wt % of the sintered bioglass, exhibited a water contact angle of 26±3°, indicating that the water contact angle, that is, the hydrophilicity of the scaffold, can be adjusted depending on the content ratio of sintered bioglass/PCL.

Test Example 6

Tissue Regeneration Applicability of Scaffold

In order to evaluate the bio-application of the scaffolds fabricated in Examples 1 to 3 and Comparative Examples 1 and 2, the analysis was carried out as follows, and the results thereof are shown below.

(1) Measurement of Protein Absorption Ability

In order to measure protein absorption ability, a BCA (Bicinchoninic acid) protein assay (Pierce Kit, Thermo Scientific) was used. Each scaffold was placed in a 24-well plate including α-minimum essential medium (Life Sciences, USA) containing 10% fetal bovine serum (Gemini Bio-Products, USA) and 1% antibiotic (Antimycotic, Cellgro, USA). Next, the scaffold was cultured at 37° C. for 1, 6, 12, and 24 hr. Before measurement of absorbance, the scaffold was cleaned with PBS (phosphate buffer saline) and lysed in 0.1% triton X-100. Next, 25 μL of the lysate was added to 200 μL of a BCA reagent. Finally, the mixture was cultured at 37° C. for 30 min. The absorbance was measured at 562 nm using a microplate reader (EL800, Bio-Tek Instruments, Winooski, Vt.).

The results of measurement of the protein absorption ability of Examples 1 to 3 and Comparative Examples 1 and 2 after 1, 6, 12 and 24 hr are shown in Table 6 below.

TABLE 6

| Absorbance (O.D.) | 1 hr | 6 hr | 12 hr | 24 hr |
|---|---|---|---|---|
| Example 1 | 0.2215 ± 0.03339 | 0.274 ± 0.00726 | 0.31167 ± 0.05856 | 0.41133 ± 0.04027 |
| Example 2 | 0.22733 ± 0.0344 | 0.2945 ± 0.000866 | 0.36433 ± 0.01872 | 0.48367 ± 0.05622 |
| Example 3 | 0.24717 ± 0.02434 | 0.3425 ± 0.03339 | 0.389 ± 0.03205 | 0.57733 ± 0.03921 |
| Comparative Example 1 | 0.28033 ± 0.01892 | 0.38967 ± 0.04119 | 0.44533 ± 0.8969 | 0.62867 ± 0.04027 |
| Comparative Example 2 | 0.179 ± 0.02498 | 0.22327 ± 0.02839 | 0.23383 ± 0.04221 | 0.24183 ± 0.02811 |

As is apparent from Table 6, compared to Comparative Example 2 using PCL alone, the scaffolds of Comparative Example 1 and Examples 1 to 3 including sintered bioglass exhibited increasing protein absorption ability over time. In particular, the protein absorption ability increased with an increase in the amount of the sintered bioglass. This is deemed to be due to the irreversible electrostatic interaction between the amine group of the protein and the negatively charged sintered bioglass component in the scaffold.

(2) Cell Activity in Scaffold in Vitro

Cell-Seeding Efficiency

The scaffold (6×6×2 $mm^3$) of each of Examples 1 to 3 and Comparative Examples 1 and 2 was sterilized with 70% ethanol under UV light. The mouse preosteoblast tissue (MC3T3-E1) was seeded at a density of $1×10^5$ cells/mL into the scaffold, after which the scaffold was placed in a 24-well plate including α-minimum essential medium (Life Sciences, USA) containing 10% fetal bovine serum (Gemini Bio-Products, USA) and 1% antibiotic (Antimycotic, Cellgro, USA). The specimen was cultured under conditions of 5% $CO_2$ and 37° C., and the medium was replaced every day.

TABLE 7

| | Cell-seeding efficiency (%) |
|---|---|
| Comparative Example 2 | 36.97689 ± 3.32317 |
| Example 1 | 45.75389 ± 2.59645 |
| Example 2 | 57.15178 ± 6.38773 |
| Example 3 | 62.14866 ± 5.10196 |

As is apparent from Table 7, the cell-seeding efficiency of the scaffold was increased with an increase in the amount of the sintered bioglass. This is deemed to be due to the protein absorption ability and biochemical properties by increasing the surface roughness and hydrophilicity of the scaffold by virtue of the sintered bioglass, indicating that, depending on the content ratio of the sintered bioglass/PCL, protein absorption ability can be improved and various cellular activities, such as initial cell adhesion, growth, and differentiation, are increased, thereby enabling control of cell adhesion ability.

Cell Proliferation Efficiency

A viable cell count was determined through a cell proliferation assay (MTT Assay) (Cell Proliferation Kit I, Boehringer Mannheim). The sample was added with 0.5 mg/mL of MTT and cultured at 37° C. for 4 hr. Thereafter, the absorbance was measured at 570 nm using a microplate reader (EL800, Bio-Tek Instruments, Winooski, Vt.).

TABLE 8

| Absorbance (O.D.) | After 1 day | After 3 days | After 7 days |
|---|---|---|---|
| Comparative Example 2 | 0.16675 ± 0.00768 | 0.1845 ± 0.0058 | 0.21375 ± 0.01053 |
| Example 1 | 0.19175 ± 0.0075 | 0.21725 ± 0.00806 | 0.25025 ± 0.01415 |
| Example 2 | 0.243 ± 0.02574 | 0.26775 ± 0.01276 | 0.334 ± 0.02099 |
| Example 3 | 0.265 ± 0.03238 | 0.2885 ± 0.02927 | 0.368 ± 0.03735 |

As is apparent from the results of MTT analysis shown in Table 8, the cell proliferation also increased with an increase in the amount of the sintered bioglass, similar to the cell-seeding efficiency of Table 6. Thereby, it can be concluded that the cell proliferation behavior can be adjusted depending on the content ratio of sintered bioglass/PCL.

F-Actin

In order to detect cell nuclei, the scaffold was exposed to fluorescent staining of Diamidino-2-phenylindole (DAPI, Invitrogen, Carlsbad, Calif.). Moreover, in order to visualize an actin cytoskeleton, staining of Phalloidin (Alexa Fluor 594; Invitrogen, Carlsbad, Calif.) was carried out, and the stained cells were observed using a confocal microscope (LSM 700; Carl Zeiss, Germany).

Figure 7:
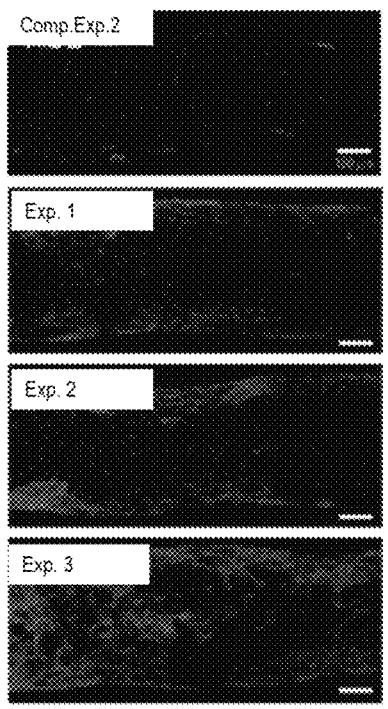
FIG. 7 is images showing blue-stained cell nuclei and red F-Actin 3 days after cell culture.

FIG. 7 shows the blue-stained cell nuclei and red F-actin 3 days after cell culture, and Table 9 below shows the F-Actin area ratio.

TABLE 9

| | F-Actin area ratio (%) |
|---|---|
| Comparative Example 2 | 21.52767 ± 2.47724 |
| Example 1 | 30.97167 ± 6.79412 |
| Example 2 | 43.029 ± 3.09069 |
| Example 3 | 53.644 ± 5.98447 |

As is apparent from FIG. 7 and Table 9, the area of F-actin was gradually increased with an increase in the amount of the sintered bioglass.

(3) Measurement of Gene Expression

In order to measure the relative expression of Type-I collagen (Col-I), Runt-related transcription factor (Runx2), Alkaline phosphatase (ALP), Osteopontin (OPN), Osteocalcin (OCN), and Bone Morphogenic Protein 2 (BMP2), real-time polymerase chain reaction of the MC3T3-E1 cells cultured for 7 days in each scaffold was carried out.

Total RNA was isolated from the cultured scaffold using a TRIzol reagent (Sigma-Aldrich), and cDNA was then synthesized therefrom. For reverse transcription, ReverTra Ace qPCR RT Master Mix (Toyobo, Japan) was used. Moreover, cDNA was amplified using THUNDERBIRD SYBR qPCR Mix (Toyobo, Japan) and ABI StepOnePlus. For amplification of cDNA, denaturation at 95° C. for 1 min was performed, after which the cycle of 15 sec at 95° C., 60 sec at 60° C., and 15 sec at 72° C. was repeated 40 times, and finally, cDNA was extended at 72° C. for 5 min.

Gene-specific primers were as follows:

```
runx2 (forward: 5'- ACATCCCCATCCATCCAT-3', reverse: 5'-GGTGCTGGGTTCTGAATCTG-3'), OPN (forward: 5'-GGAGGAAACCAGCCAAGG-3', reverse: 5'-TGCCAGAATCAGTCACTTTCAC-3'), OCN (forward: 5'-CCCTCCTGAAGGTCTCACAA-3', reverse: 5'-GCTGTCTCCCTCATGTGTTG-3'), Col-I (forward: 5'-ACTCAGCCGTCTGTGCCTCA-3', reverse: 5'-GGAGGCCTCGGTGGACATTA-3'), ALP (forward: 5'-GCCCAGTGCCTTCTGATTT-3', reverse: 5'-GGGCAGCGTCAGATGTTAAT-3'), BMP2 (forward: 5'-AGA TCT GTA CCG CAG GCACT-3', reverse: 5'-GTTCCTCCACGGCTTCTTC-3'), and the housekeeping gene mouse GAPDH (forward: 5'-CCTTGAGATCAACACGTACCAG-3', reverse: 5'-CGCCTGTACACTCCACCAC-3').
```

TABLE 10

| | No. | Relative expression |
|---|---|---|
| ALP/GAPDH | Comparative Example 2 | 1 ± 0.22087 |
| | Example 1 | 1.33828 ± 0.38901 |
| | Example 2 | 2.77655 ± 0.09479 |
| | Example 3 | 3.58484 ± 0.40055 |
| BMP-2/GAPDH | Comparative Example 2 | 1 ± 0.35537 |
| | Example 1 | 2.9804 ± 0.58307 |
| | Example 2 | 4.81805 ± 0.66508 |
| | Example 3 | 6.10637 ± 0.86176 |
| Col/GAPDH | Comparative Example 2 | 1 ± 0.06532 |
| | Example 1 | 13.14175 ± 0.60236 |
| | Example 2 | 18.40076 ± 0.88642 |
| | Example 3 | 21.20035 ± 1.86857 |
| OPN/GAPDH | Comparative Example 2 | 1 ± 0.04191 |
| | Example 1 | 3.93551 ± 0.31252 |
| | Example 2 | 10.18773 ± 0.5399 |
| | Example 3 | 13.43262 ± 3.01044 |
| RUNX-2/GAPDH | Comparative Example 2 | 1 ± 0.13509 |
| | Example 1 | 18.59516 ± 0.55741 |
| | Example 2 | 40.86318 ± 5.59465 |
| | Example 3 | 48.70381 ± 10.47568 |
| OCN/GAPDH | Comparative Example 2 | 1 ± 0.02964 |
| | Example 1 | 1.27795 ± 0.06102 |
| | Example 2 | 2.40561 ± 0.24953 |
| | Example 3 | 3.0789 ± 0.22572 |

As is apparent from Table 10, in the scaffolds of Examples 1 to 3 and Comparative Examples 1 and 2, the extent of gene expression was also increased with an increase in the amount of the sintered bioglass. Thereby, it can be concluded that the bioglass affects bone formation, differentiation and biological activity and that it is necessary to control the content ratio of sintered bioglass/PCL in order to ensure high gene expression levels.

Test Example 7

Optimal Content Ratio of Sintered Bioglass/PCL

The toughness, cell-seeding efficiency, cell proliferation rate, and Runt-related transcription factor of the scaffolds for living donor transplantation fabricated in Examples and Comparative Examples were evaluated and plotted, and respective optical images thereof are represented.

Figure 8:
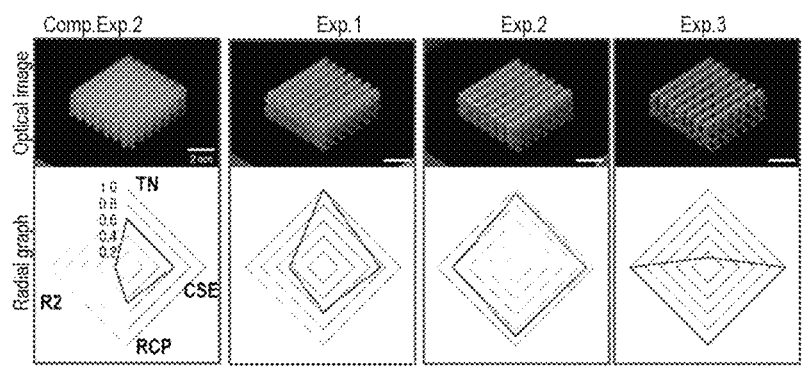
FIG. 8 shows the results of comprehensive evaluation of the scaffolds of Comparative Example 1 and Examples 1 to 3.

FIG. 8 shows the results of comprehensive evaluation of the scaffolds of Comparative Example 2 and Examples 1 to 3. As shown in FIG. 8, the scaffolds of Examples 1 to 3 containing both sintered bioglass and PCL exhibited properties superior to those of Comparative Example 2. In particular, the scaffolds of Examples 1 and 2, especially the scaffold of Example 2, exhibited the most desirable results in the overall evaluation.

What is claimed is:

1. A scaffold for living donor transplantation, configured such that struts, which are disposed on top of each other and cross each other in a vertical direction to thus form pores therein, are stacked layer by layer,
wherein the struts include 10 to 70 wt % of sintered bioglass and 30 to 90 wt % of a biocompatible polymer,
wherein the struts are configured such that sintered bioglass particles are dispersed in a biocompatible polymer matrix,
wherein the scaffold is fabricated by mixing the sintered bioglass and the biocompatible polymer and then performing injection molding, and
wherein the scaffold has a toughness of 50 kPa/mm' to 850 kPa/mm' and a stiffness of 1.5 N/mm to 20 N/mm.

2. The scaffold of claim 1, wherein the sintered bioglass particles have an average particle size of 1.5 to 2.5 μm.

3. The scaffold of claim 1, wherein the struts have a diameter of 300 μm to 500 μm.

4. The scaffold of claim 1, wherein the struts have a stack structure of two or more layers.

5. The scaffold of claim 1, wherein the struts are provided in an interconnected or disconnected form in a same layer and are formed parallel in a regular pattern including a linear shape, a corrugated shape, a lattice shape, a zigzag shape or a spiral shape, or in an irregular pattern.

6. The scaffold of claim 1, wherein the struts have an average orientation angle of 30° to 60° between layers.

7. The scaffold of claim 1, wherein the scaffold has a bimodal pore size distribution and a porosity of 30% to 60%.

8. The scaffold of claim 1, wherein the scaffold has a roughness (Ra) of 130 nm to 260 nm and a water contact angle of 75° or less after 180 sec.

9. The scaffold of claim 1, wherein a protein proliferation absorbance after 24 hr is 0.25 O.D. (optical density) or more, a cell-seeding efficiency is 37% or more, a cell proliferation absorbance after culture for 7 days is 0.22 O.D. or more, and an F-actin area ratio is 22% or more.

10. The scaffold of claim 1, wherein the injection molding is performed using a 3D printer through a fused deposition modeling process.

\* \* \* \* \*